US006723878B2

(12) United States Patent
Laitinen

(10) Patent No.: US 6,723,878 B2
(45) Date of Patent: Apr. 20, 2004

(54) METHOD FOR PREPARING SERTRALINE

(75) Inventor: Ilpo Laitinen, Espoo (FI)

(73) Assignee: Orion Corporation Fermion, Espoo (FI)

( * ) Notice: Subject to any disclaimer, the term of this patent is extended or adjusted under 35 U.S.C. 154(b) by 0 days.

(21) Appl. No.: 10/170,576

(22) Filed: Jun. 14, 2002

(65) Prior Publication Data

US 2003/0050509 A1 Mar. 13, 2003

Related U.S. Application Data

(60) Provisional application No. 60/298,088, filed on Jun. 15, 2001.

(51) Int. Cl.$^7$ ............................................. C07C 211/00
(52) U.S. Cl. ....................................... 564/308
(58) Field of Search .......................... 564/308

(56) References Cited

U.S. PATENT DOCUMENTS

| 3,474,144 | A | 10/1969 | Craig et al. |
| 4,020,107 | A | 4/1977 | Kosak |
| 4,536,518 | A | 8/1985 | Welch, Jr. et al. |
| 4,556,676 | A | 12/1985 | Welch, Jr. et al. |
| 5,019,655 | A | 5/1991 | Adrian |
| 5,082,970 | A | 1/1992 | Braish |
| 6,232,500 | B1 | 5/2001 | Colberg et al. |
| 6,262,308 | B1 | 7/2001 | Bigot |

FOREIGN PATENT DOCUMENTS

| CA | 2310799 | 12/2000 |
| EP | 0 292 682 | 11/1988 |
| EP | 0 947 499 | 10/1999 |
| WO | WO 99/47486 | 9/1999 |
| WO | WO 99/57093 | 11/1999 |
| WO | WO 01/09080 | 2/2001 |
| WO | WO 01/16089 | 3/2001 |
| WO | WO 01/36377 | 5/2001 |
| WO | WO 0136378 | 5/2001 |
| WO | WO 01/49638 | 7/2001 |
| WO | WO 01/68566 | 9/2001 |

OTHER PUBLICATIONS

J.R. Kosak, *Catalysis in Organic Syntheses*, volume date 1978, pp. 107–117, 1980.
International Search Report for Interantional Application No. PCT/FI02/00518.
Office Action for Finnish Application No. 20011271.

*Primary Examiner*—Samuel Barts
(74) *Attorney, Agent, or Firm*—Oblon, Spivak, McClelland, Maier & Neustadt, P.C.

(57) ABSTRACT (1S-cis)-4-(3,4-dichlorophenyl)-1,2,3,4-tetrahydro-N-methyl-1-naphthalenamine (sertraline) may be prepared by hydrogenating of N-[4-(3,4-dichlorophenyl)-3, 4-dihydro-1 (2H)-naphthalenylidene]methanamine in the presence of a dehalogenation inhibitor, e.g., triphenylphosphite or trimethylphosphite and a catalyst.

17 Claims, No Drawings

METHOD FOR PREPARING SERTRALINE

CROSS REFERENCE TO RELATED APPLICATIONS

This application claims priority to U.S. Provisional Application Ser. No. 60/298,088, which was filed on Jun. 15, 2001, and which is incorporated herein by reference in its entirety.

BACKGROUND OF THE INVENTION

1. Filed of the Invention

The present invention relates to a novel process for the preparation of (1S-cis)-4-(3,4-dichlorophenyl)-1,2,3,4-tetrahydro-N-methyl-1-naphthalenamine(sertraline) comprising hydrogenation of N-[4-(3,4-dichlorophenyl)-3,4-dihydro-1(2H)-naphthalenylidene]methanamine.

2. Discussion of the Background

Sertraline, (1S-cis)-4-(3,4-dichlorophenyl)-1,2,3,4-tetrahydro-N-methyl-1-naphthalenamine, which has a structure of formula I

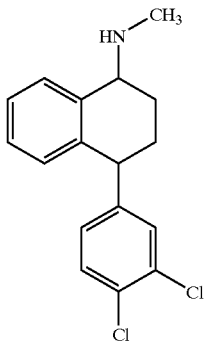

is marketed in the form of its hydrochloride for the treatment of depression, obsessive-compulsive disorder and panic disorder.

The synthesis of sertraline is described in U.S. Pat. No. 4,536,518, which is incorporated herein by reference. The process described comprises a condensation reaction of 4-(3,4-dichlorophenyl)-3,4-dihydro-1(2H)-naphthalenone of formula II with

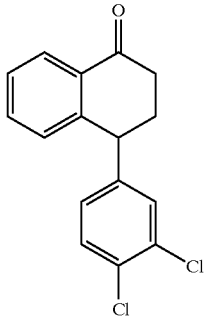

monomethylamine yielding N-[4-(3,4-dichlorophenyl)-3,4-dihydro-1(2H)-naphthalenylidene]methanamine. This is further hydrogenated in the presence of palladium on carbon catalyst to form a mixture of cis- and trans-racemates of 4-(3,4-dichlorophenyl)-1,2,3,4-tetrahydro-N-methyl-1-naphthalenamine with the isomeric ratio of 70:30. The desired product is the cis isomer, and accordingly the trans isomer is a not desired by-product which is classified as an impurity in the final product. Other impurities formed in the reaction are, e.g., dehalogenation products, the amount of which depends, e.g., on the temperature and pressure used in the hydrogenation and the quality of the imine starting material. The removal of the dehalogenation products is difficult.

Different solutions have been suggested to increase the formation of the cis isomer and to prevent the dehalogenation reaction in the hydrogenation. In the process described in U.S. Pat. No. 5,082,970, the trans-isomer is treated with a basic equilibration agent like potassium tert-butoxide to convert it to the cis-isomer. This approach, however, requires an additional step in the synthesis. In WO 99/47486, copper containing catalysts are used to improve the ratio, and results as high as 98.5% in favor of the cis compound have been achieved. Nothing has, however, been said about the dehalogenation products formed. In WO 99/57093, a hydrogenation process with a palladium catalyst which has been pretreated with alkali halide has been described. The process described gives a cis/trans ratio of 85–95/15–5 (in %), and the amount of dehalogenation side products is said to be below 0.5%.

In U.S. Pat. No. 3,474,144, there has been described the use of triphenyl phosphite or tritolyl phosphite as dehalogenation inhibitors in the catalytic reduction of aromatic chloronitro compounds. It has also been mentioned that the use of the inhibitors does not affect the original isomer ratio. EP 292 682 discloses the use of organic esters of phosphoric acid together with hydrocarbyl-silanes to inhibit the dehalogenation during the catalytic reduction of aromatic nitrohalo-derivatives. A degree of dehalogenation lower than 1% was reported. In Kosak, *Catal. Org. Synth.*, 1980, vol. date 1978, p. 107–117, there has been described the use of phosphorous acid and some related compounds as dehalogenation inhibitors in the hydrogenation of haloaromatic nitro compounds. However, the use of the inhibitors of the present invention in the preparation of sertraline or in the hydrogenation of imine compounds has not been described.

SUMMARY OF THE INVENTION

Accordingly, it is one object of the present invention to provide an improved preparation method for cis-sertraline and/or a pharmaceutically acceptable acid addition salt thereof.

It is another object of the present invention to provide an improved preparation method for cis-sertraline and/or a pharmaceutically acceptable acid addition salt thereof, which affords sertraline having a high content of the cis isomer.

It is another object of the present invention to provide an improved preparation method for cis-sertraline and/or a pharmaceutically acceptable acid addition salt thereof, which produces the undesirable dehalogenated side products in a reduced amount.

It is another object of the present invention to provide pharmaceutical compositions comprising cis-sertraline or a pharmaceutically acceptable acid addition salt thereof made by the process of the invention.

These and other objects, which will become apparent during the following detailed description, have been achieved by the inventor's surprising discovery that if some phosphorus compounds, especially esters of phosphorous acid, are used as dehalogenation inhibitors in the hydrogenation of the imine in the production of sertraline, the cis-trans ratio is improved. In addition, the amount of dehalogenation products is diminished. The produced racemic cis-sertraline can be further resolved or crystallized directly to a pharmaceutically acceptable acid addition salt, e.g., hydrochloride.

DETAILED DESCRIPTION OF THE PREFERRED EMBODIMENTS

The present invention provides a process for the preparation of cis-sertraline comprising hydrogenating N-[4-(3,4-dichlorophenyl)-3,4-dihydro-1(2H)-naphthalenylidene] methanamine in the presence of a catalyst and a dehalogenation inhibitor to obtain cis-racemate of 4-(3,4-dichlorophenyl)-1,2,3,4-tetrahydro-N-methyl-1-naphthalenamine.

By using the hydrogenation process of the present invention, the ratio of cis:trans isomers is improved to as high as 97:3, and the formation of the dehalogenation by-products may be reduced to even less than 0.1%. No further purification process is needed before resolution or crystallization. These results are achieved by using the inhibitors of the invention in the hydrogenation process.

Cis-sertraline is prepared starting from 4-(3,4-dichlorophenyl)-3,4-dihydro-1-(2H)-naphthalenone (tetralone), which can be prepared by methods known in the art, e.g., as described in U.S. Pat. No. 5,019,655, which is incorporated herein by reference in its entirety. Tetralone is then reacted with monomethylamine to form an imine, which can be performed by methods known in the art, e.g., as described in U.S. Pat. No. 4,536,518, which is incorporated herein by reference in its entirety. The imine obtained is further hydrogenated to the cis-racemate of 4-(3,4-dichlorophenyl)-1,2,3,4-tetrahydro-N-methyl-1-naphthalenamine in the presence of a catalyst and a dehalogenation inhibitor of the invention. From this mixture, the cis-compound can be either resolved by, e.g., mandelic acid or 10-camphorsulphonic acid to afford cis-(+)-sertraline and crystallized as a base or a pharmaceutically acceptable acid addition salt, e.g., hydrochloride, or the racemic cis-sertraline can be crystallized as a base or as a pharmaceutically acceptable salt.

The hydrogenation of the imine is performed in the presence of a catalyst and an inhibitor, which is selected from the group consisting of hypophosphorous acid, esters of hypophosphorous acid, phosphorous acid, esters of phosphorous acid, phosphine and substituted phosphines. Suitable inhibitors are, e.g., mono-, di-, and triesters of phosphorous acid, preferably trimethyl phosphite, triphenyl phosphite, or tritolyl phosphite. Examples suitable phosphines are, e.g., trimethylphosphine, triethylphosphine, triisopropylphosphine, tritolylphosphine, and tribenzylphosphine. The amount of the inhibitor used in the process is typically 0.5–10 mol %, preferably 3–5 mol %, based on the number of moles of the metal in the catalyst used.

The catalyst used can be any suitable catalyst known in the art, e.g., palladium on carbon, palladium on graphite, palladium on carbon paste or $PtO_2$. The catalyst is typically used in an amount of 0.1–1.0% (w/w, calculated as the pure metal in the catalyst) based on the weight of the imine used. The hydrogenation may be carried out in an organic solvent, which can be any suitable protic or aprotic solvent or mixtures thereof. Examples of solvents are, e.g., dimethylformamide (DMF), esters like ethyl acetate, chlorinated hydrocarbons like methylene chloride or chloroform, or alcohols like methanol, ethanol or isopropanol. Preferably a lower alcohol, e.g., methanol or ethanol or their mixtures with DMF is used as the solvent.

The reaction can be carried out at a temperature of 0–100° C., preferably at 20–50° C. The hydrogen pressure used is typically from 1 to 50 bar, preferably from 2 to 5 bar.

The reaction time can vary from half an hour to 24 hours depending on the catalyst used, on hydrogen pressure, on the reaction temperature and on the equipment used. Preferably the hydrogenation time is about 2 to 6 hours.

The following examples merely illustrate the invention and they are not to be construed as limiting.

EXAMPLES

Example 1

Cis-(1S)(1R)-4-(3,4-dichlorophenyl)-1,2,3,4-tetrahydro-N-methyl-1-naphthalenamine.

N-[4-(3,4-dichlorophenyl)-3,4-dihydro-1-(2H)-naphthalenylidene]-methanamine (50 g), methanol (300 ml), palladium on graphite 5% (2.5 g), and trimethyl phosphite (0.004 g) are charged into a reaction vessel. The mixture is hydrogenated at 5 bar overpressure of hydrogen for 5 hours at about 40° C. The catalyst is removed by filtration, and the cake is washed with methanol. The cis:trans ratio is 97:3. The amount of dehalogenation byproducts is <0.1%. The reaction mixture can be used directly in the resolution step or crystallized as the HCl salt.

Example 2

(1S-cis)-4-(3,4-dichlorophenyl)-1,2,3,4-tetrahydro-N-methyl-1-naphthalenamine Hydrochloride (Sertraline Hydrochloride).

The reaction mixture containing the racemic compound from the previous step is resolved by mandelic acid and finally crystallized as sertraline hydrochloride. The total yield is 19.8 g (70% of theoretical (+)-enantiomer). Analytical results: HPLC-purity is 99.9%, trans-isomer <0.1% and dehydrohalogenation products <0.1%. Optical purity is 99.9%.

Example 3

Cis-(1S)(1R)-4-(3,4-dichlorophenyl)-1,2,3,4-tetrahydro-N-methyl-1-naphthalenamine.

N-[4-(3,4-Dichlorophenyl)-3,4-dihydro-1(2H)-naphthalenylidene]methanamine (40 g), dimethylformamide (150 ml), methanol (150 ml), palladium on graphite catalyst (4 g), and triphenyl phosphite (0.0010 g) are charged into a reaction vessel. The mixture is hydrogenated for 5 hours under 5 bar overpressure of hydrogen at 20–25° C. The catalyst is removed by filtration, and the cake washed with methanol. The cis:trans ratio is 96:4, and the amount of dehalogenation by-products is 0.5%.

Example 4

Cis-(1S)(1R)-4-(3,4-dichlorophenyl)-1,2,3,4-tetrahydro-N-methyl-1-naphthalenamine.

N-[4-(3,4-dichlorophenyl)-3,4-dihydro-1-(2H)-naphthalenylidene]-methanamine (50 g), methanol (400 ml), palladium on graphite 5% (5 g), and triphenyl phosphine (0.014 g) are charged into a reaction vessel. The mixture is hydrogenated at 5 bar overpressure of hydrogen for 3 hours at about 35° C. The catalyst is removed by filtration, and the cake is washed with methanol. The cis:trans ratio is 97:3. The amount of dehalogenation byproducts is 0.2%. The reaction mixture can be used directly in the resolution step or crystallized as HCl salt.

Obviously, numerous modifications and variations of the present invention are possible in light of the above teachings. It is therefore to be understood that, within the scope of the appended claims, the invention may be practiced otherwise than as specifically described herein.

What is claimed is:

1. A process for the preparation of cis-sertraline, comprising hydrogenating N-[4-(3,4-dichlorophenyl)-3,4-dihydro-1(2H)-naphthalenylidene]methanamine in the presence of a catalyst and a dehalogenation inhibitor, to obtain cis-racemate of 4-(3,4-dichlorophenyl)-1,2,3,4-tetrahydro-N-methyl-1-naphthalenamine.

2. The process of claim 1, wherein the dehalogenation inhibitor is selected from the group consisting of hypophosphorous acid, esters of hypophosphorous acid, phosphorous acid, esters of phosphorous acid, phosphine, and substituted phosphines.

3. The process of claim 1, wherein said dehalogenation inhibitor is an ester of phosphorous acid.

4. The process of claim 3, wherein said dehalogenation inhibitor is selected from the group consisting of triphenyl phosphite, trimethyl phosphite, and tritolyl phosphite.

5. The process of claim 1, wherein the dehalogenation inhibitor is used in amount of 0.5 to 10.0 mol %, based on the number of moles of metal in said catalyst.

6. The process of claim 2, wherein the dehalogenation inhibitor is used in amount of 0.5 to 10.0 mol %, based on the number of moles of metal in said catalyst.

7. The process of claim 3, wherein the dehalogenation inhibitor is used in amount of 0.5 to 10.0 mol %, based on the number of moles of metal in said catalyst.

8. The process of claim 4, wherein the dehalogenation inhibitor is used in amount of 0.5 to 10.0 mol %, based on the number of moles of metal in said catalyst.

9. The process of claim 5, wherein the dehalogenation inhibitor is used in an amount of 3 to 5 mol %, based on the number of moles of metal in said catalyst.

10. The process of claim 1 wherein said catalyst is a palladium or a platinum catalyst.

11. A process for the preparation of (1S-cis)-4-(3,4-dichlorophenyl)-1,2,3,4-tetrahydro-N-methyl-1-naphthalenamine or an acid addition salt thereof, comprising:

hydrogenating N-[4-(3,4-dichlorophenyl)-3,4-dihydro-1(2H)-naphthalenylidene]methanamine in the presence of a catalyst and a dehalogenation inhibitor, to obtain cis-racemate of 4-(3,4-dichlorophenyl)-1,2,3,4-tetrahydro-N-methyl-1-naphthalenamine; and resolving said cis-racemate of 4-(3,4-dichlorophenyl)-1,2,3,4-tetrahydro-N-methyl-1-naphthalenamine, to obtain the (+)enantiomer of cis-4-(3,4-dichlorophenyl)-1,2,3,4-tetrahydro-N-methyl-1-naphthalenamime.

12. The process of claim 11, further comprising crystallizing said (+)enantiomer of cis-4-(3,4-dichlorophenyl)-1,2,3,4-tetrahydro-N-methyl-1-naphthalenamine as a base or as an acid addition salt.

13. The process of claim 12, wherein said acid addition salt is a hydrochloride.

14. The process of claim 11, wherein said dehalogenation inhibitor is selected from the group consisting of hypophosphorous acid, esters of hypophosphorous acid, phosphorous acid, esters of phosphorous acid, phosphine, and substituted phosphines.

15. The process of claim 14, wherein said dehalogenation inhibitor is an ester of phosphorous acid.

16. The process of claim 15, wherein said dehalogenation inhibitor is selected from the group consisting of triphenyl phosphite, trimethyl phosphite, and tritolyl phosphite.

17. The process of claim 11, wherein the dehalogenation inhibitor is used in amount of 0.5 to 10.0 mol %, based on the number of moles of metal in said catalyst.

* * * * *